United States Patent [19]

Caboche

[11] Patent Number: 5,620,871
[45] Date of Patent: Apr. 15, 1997

[54] PROCESS FOR PREPARING OPTIONALLY HYDROGENATED INDIGESTIBLE POLYSACCHARIDES

[75] Inventor: Jean-Jacques Caboche, Bethune, France

[73] Assignee: Roquette Ferres, Lestrem, France

[21] Appl. No.: 390,369

[22] Filed: Feb. 16, 1995

Related U.S. Application Data

[63] Continuation of Ser. No. 998,630, Dec. 30, 1992, abandoned.

[30] Foreign Application Priority Data

Mar. 19, 1992 [FR] France ................... 92 03313

[51] Int. Cl.$^6$ ................. C12P 19/22; C12P 19/20
[52] U.S. Cl. ................. 435/95; 435/96; 435/99; 435/100; 435/101; 536/103; 536/123.1; 127/29; 127/38
[58] Field of Search ................. 435/95, 101, 96, 435/99, 100; 536/103, 123.1; 127/29, 38

[56] References Cited

U.S. PATENT DOCUMENTS

| | | | |
|---|---|---|---|
| 2,436,967 | 3/1948 | Leuck | 536/124 |
| 3,766,165 | 10/1973 | Rennhard | 536/1.11 |
| 4,346,116 | 8/1982 | Verwaerde et al. | 426/48 |
| 4,965,354 | 10/1990 | Yanaki et al. | 536/4.1 |
| 5,051,500 | 9/1991 | Elmore | 536/124 |

FOREIGN PATENT DOCUMENTS

| | | |
|---|---|---|
| 0063909 | 4/1982 | European Pat. Off. . |
| 0257535 | 8/1987 | European Pat. Off. . |
| 0368451 | 9/1989 | European Pat. Off. . |
| 01-12761 | 10/1985 | Japan . |
| 02-163101 | 12/1988 | Japan . |
| 9202614 | 7/1991 | WIPO . |

OTHER PUBLICATIONS

The Merck Index, 11th Ed., p. 465 (1989).
Sigma Technical note n° TDFAB-1, Jun. 1991.
"J. Assoc. Off. Anal. Chem." vol. 68, N° 2, 1985, p. 399.
"Starch chemistry and technology"—Second Edition, Edited by Roy L. Whistler, 1984, Academic Press Inc.
Denpun Kagaku, 1989, 36(4), 283–6 (Japan)—Kobayashi T. and Yoshino H.

*Primary Examiner*—John W. Rollins
*Assistant Examiner*—Francisco C. Prats
*Attorney, Agent, or Firm*—Larson & Taylor

[57] ABSTRACT

The present invention relates to a process for preparing indigestible polysaccharides and to the corresponding hydrogenated products. This process essentially consists in carrying out an enzymatic hydrolysis of at least one dextrin and/or one polyglucose using at least one saccharifying enzyme and at least one enzyme which hydrolyzes the 1–6 bonds of amylopectin.

15 Claims, No Drawings

PROCESS FOR PREPARING OPTIONALLY HYDROGENATED INDIGESTIBLE POLYSACCHARIDES

This application is a continuation of application Ser. No. 07/998,630 filed Dec. 30, 1992, now abandoned.

The present invention relates to a process for preparing indigestible polysaccharides and to the corresponding hydrogenated products.

During the last decade, increasingly high interest has been shown in the consumption of food fibers or products having an effect similar to that of food fibers, in order to improve intestinal transit especially in the inhabitants of highly developed countries for whom food products are increasingly processed and therefore contain fewer and fewer natural fibers.

The daily or practically daily consumption of food fibers is also reputed to decrease the frequency of cancers of the colon.

This being the case, the production of very highly processed or extremely pure food fibers is not always easy to achieve and the insoluble fibers obtained from plant products can sometimes have an adverse effect, that is to say cause irritation of the colon and thereby have detrimental effects on the intestinal mucous membranes.

Attention has therefore been increasingly focused on the production of soluble fibers. One of the many lines of research in this field has been to produce said soluble fibers by hydrolysis of starchy materials or by rearrangement of products derived from said starchy materials.

Thus, for example, a product commonly called polydextrose was manufactured about twenty years ago, this product being obtained by rearrangement of glucose molecules by heating under relatively anhydrous conditions in the presence of food acids, a small amount of sorbitol also being present in the reaction medium.

However, this polydextrose, reputed to have a calorific value of about one calorie per gram, suffers from many disadvantages, in particular because of its relatively unpleasant taste and its tendency to become colored; furthermore, it does not possess all the qualities required for a food fiber.

Given the process for its manufacture, this product in fact constitutes a poorly defined mixture of very different products with very diverse molecular masses. It is thus most commonly characterized by a mean molecular mass only partially reflecting the molecular mass of all the molecules in its composition. The presence in this product of bitter and sour compounds greatly limits its applications.

Another process already described in the literature consisted in converting starch to a dextrin containing bonds different from those found in the original starch, and then in hydrolyzing this dextrin using an $\alpha$-amylase, this $\alpha$-amylase action being optionally completed by the action of other enzymes. Such an approach has thus for example been described in Patent Application EP No. 0,368,451.

One of the essential advantages of the process described in the abovementioned patent application is the ability, by virtue of the enzymatic action of $\alpha$-amylase, to remove or very substantially reduce the unpleasant taste and odor from the initial dextrin. However, the products obtained according to this process are not as indigestible as might be desired. Their quality as soluble food fibers is therefore far from being optimal.

The object of the present invention is to provide a process which makes it possible to manufacture very simply, from dextrins obtained from starch, soluble food fibers which are much less digestible than all those proposed in the prior art and which thereby make it possible to obtain a completely optimal food fiber effect.

The process for preparing indigestible polysaccharides conforming to the invention comprises the enzymatic hydrolysis of at least one dextrin and/or one polyglucose using at least one saccharifying enzyme and at least one enzyme which hydrolyzes the 1–6 bonds of amylopectin.

It is essentially by virtue of the action of the enzyme hydrolyzing the 1–6 bonds of amylopectin that the polysaccharides obtained at the end of this process possess a minimal digestibility.

Surprisingly, it has furthermore been observed that the process for preparing indigestible polysaccharides conforming to the invention also makes it possible to obtain a product having excellent organoleptic qualities, without necessarily having to resort to the use of $\alpha$-amylase as recommended in the prior art. The product thus obtained is particularly neutral in taste, colorless, odorless and is not bitter. Finally, it is very highly stable to microbial enzymes.

The indigestible polysaccharides can be prepared according to the process conforming to the invention by carrying out the procedure as follows or in a similar manner.

A dextrin obtained from starch is dispersed or solubilized in water to a dry matter content generally of between 20 and 70% and preferably of between 20 and 45%.

The suspension thus obtained is then subjected to an enzymatic treatment comprising at least the action of one saccharifying enzyme and one enzyme hydrolyzing the 1–6 bonds of amylopectin, the conditions for this enzymatic treatment being chosen such that the DE (Dextrose Equivalent) of the hydrolysate obtained is between 5 and 80, preferably between 7 and 60, and still more preferably between 10 and 50.

This process also makes it possible to prepare indigestible polysaccharides from polyglucose or mixtures of dextrin and polyglucose.

The enzymatic hydrolysis of polyglucoses, in particular of polydextrose, has already been achieved, but using glucoamylases such as $\alpha$-amylase, isomaltodextranase, glucodextranase and glucoamylase, and this with a purely analytical objective for the purpose of determining the characteristic structure of polydextrose. The work on this subject by Kobayashi T. and Yoshino H. (Denpun Kagaku, 1989, 36 (4), 283–6 (Japan)) may in particular be mentioned.

To the knowledge of the applicant, it had never been envisaged until now to hydrolyse polyglucoses using enzymes which hydrolyse the 1–6 bonds of amylopectin, such as isoamylase and pullulanase, and thus to prepare polysaccharides having a completely optimal food fiber effect.

The term "polyglucose", within the context of the present invention, is understood to mean the products predominantly composed of 1–6 bonds, obtained by condensation or rearrangement, from glucose or from one or more optionally reduced sugars, under the combined action of heat and acids in a medium practically devoid of water. Such polymers have been described many times and can be obtained by processes such as those described in particular in Patents U.S. Pat. No. 2,436,967, U.S. Pat. No. 3,766,165, U.S. Pat. No. 4,965,354, U.S. Pat. No. 5,051,500, JP 01-12761 and JP 02-163101. Advantageously, these polymers, such as the above-mentioned polydextrose type products, are obtained from glucose and citric acid, optionally in the presence of sorbitol.

The term "dextrin" is understood to mean the products obtained by heating starch adjusted to a low moisture level, generally in the presence of acidic or basic catalysts. This "dry roasting" of starch, most commonly in the presence of an acid, brings about both depolymerization of the starch and rearrangement of the starch fragments obtained, resulting in the production of highly branched molecules.

Dextrins are among the oldest starch derivatives and their preparation, their applications, the various types of dextrins as well as their properties are described for example in the book entitled "Starch Chemistry and Technology"—Second Edition—Edited by Roy L. WHISTLER—1984—Academic Press Inc.

Preferably, dextrins obtained by dry roasting of starch in the presence of an acidic catalyst such as hydrochloric acid are used for the preparation of the polysaccharides conforming to the invention. The acid, in the form of a dilute solution, is thus sprayed over the starch and the mixture obtained is predried, for example from 80° to 130° C. until a water content of less than or equal to about 5% is obtained. The mixture is then "roasted" at a temperature of about 140° to 250° C. for a period of 30 minutes to about 6 hours in order to obtain the dextrin, which has at the end of the reaction a DE of about 0.5 to 10. Any type of starch, and in particular maize starch, potato flour, wheat starch, cassava flour, rice starch and pea starch can be used for the preparation of these dextrins.

According to the standard ISO 1227 of 1979, a dextrin is obtained from starch or starch flour converted by heating in the dry state with or without the addition of small amounts of chemical reagents. Traditionally, dextrins are classified into two categories: white dextrins whose appearance is not very different from that of the raw material used, and yellow dextrins which are produced under more drastic conditions and whose depth of color can be correlated with the degree of modification of the native structure. The four types of reaction occurring during the dextrinization are, at low temperatures, essentially hydrolysis of the alpha 1–4 bonds, and then at higher temperatures, condensation, transglycosidation resulting in a rearrangement, and finally anhydrization reactions.

Dextrins such as those marketed by the applicant company under the trademarks TACKIDEX DF 165, TACKIDEX DF 155, TACKIDEX JO 55 K may be advantageously used.

The hydrolysate obtained after the saccharification and the action of the enzyme hydrolyzing the 1–6 bonds of amylopectin is then purified in a manner known per se by decolorization over activated carbon and demineralization over ion exchange resins. The hydrolysates may also be decolorized using oxidizing or reducing agents.

The product obtained may then be optionally hydrogenated, also in a manner known per se, for example over a Raney nickel catalyst or over noble metal catalysts.

A product is obtained in this manner which is still stable to boiling and storage, has a reduced chemical reactivity and also the important property of not being cariogenic.

The saccharifying enzyme used in conformity with the process of the present invention is preferably chosen from β-amylase and amyloglucosidase, it being possible however for these two enzymes to be used simultaneously or successively.

Preferably, the amounts and conditions for the action of these various saccharifying enzymes which may be used for preparing the indigestible polysaccharides conforming to the invention, are chosen from the following:

β-amylase: 100 to 10,000 LINTNER units/kg of dry substrate, temperature of 50° C. to 60° C. duration of action from 30 to 100 hours, pH of 5.0 to 6.0 amyloglucosidase: 4,000 to 500,000 international units/kg of dry substrate, temperature of 50° C. to 60° C., and duration of action from 30 to 100 hours, pH of 5.0 to 6.0.

In the case of the enzymes which hydrolyze the 1–6 bonds of amylopectin, they are chosen from pullulanase and isoamylase, it being thus possible for commercial enzymes such as PULLUZYME 750 L from the company ABM or CK 20 L from the company AMANO or PROMOZYME from the company NOVO to be used. The amounts and conditions for the action of these enzymes are as follows:

150 to 15,000 ABM units (the company ABM, CHESHIRE, ENGLAND) per kg of dry substrate, pH of 5.0 to 6.0, temperature of 50° C. to 60° C. duration of action from 24 to 100 hours.

The hydrolysis of dextrin and/or polyglucose using a saccharifying enzyme and an enzyme which hydrolyzes the 1–6 bonds of amylopectin may be optionally preceded, accompanied or followed by an additional action using an α-amylase, or may be optionally preceded by an acid hydrolysis.

In the case of this latter possibility, it can be stated that it is not absolutely essential to add an amount of acid to the dextrin, the latter containing at the end of the actual dextrinization step a residual amount of acid sufficient to ensure acid hydrolysis of the insoluble or partially dextrinized starch.

Consequently, the action of an α-amylase prior to the enzymatic action of the saccharifying enzymes and the enzymes which hydrolyze the 1–6 bonds of amylopectin is not generally required.

On the other hand, the action of an α-amylase can sometimes prove useful following the action of the saccharifying enzyme and the enzyme hydrolyzing the alpha 1–6 bonds.

In the case where α-amylase is used in the process conforming to the invention, bacterial or fungal α-amylases are preferably used, and the conditions and amounts for the action of the α-amylase are generally as follows:

20 to 2,000 KNU units (Kilo Novo Units)/kg of dry substrate, pH of 5.0 to 6.0, temperature of 50° C. to 60° C., duration of action from 16 to 100 hours.

Hydrogenation of the product obtained following enzymatic hydrolysis of dextrin and/or polyglucose may be carried out in a manner known per se, by hydrogenation over Raney nickel or by hydrogenation over noble metals. This hydrogenation is carried out after purification of the product, for example by treatment over activated carbon, followed by demineralization over cationic and anionic resins. The hydrogenation may be carried out for example over a Raney nickel catalyst, at a temperature of 130° C. and at a hydrogen pressure of 50 bars.

After hydrogenation, the hydrogenated product obtained is filtered, demineralized and then concentrated until the commercial concentration is obtained, which is generally between about 40 and 70 Brix. It is recalled that the Brix is a unit of measurement commonly used in the starch industry, and that the Brix of a syrup is determined very easily by a refractometer reading. A Brix of about 75 corresponds, for the products to which the invention relates, to a dry matter content of about 70%.

The hydrogenation is carried out until a percentage ratio of residual reducing sugars to dry matter of less than 2.0, preferably less than 1.0 and still more preferably less than 0.25, is obtained.

The products obtained following the enzymatic hydrolysis of dextrin and/or polyglucose, whether they are hydrogenated or otherwise, may also be provided in pulverulent form, it being possible for this pulverulent form to be obtained for example by spray-drying.

It may sometimes be desirable to increase the indigestible polysaccharide concentration of the product obtained at the end of the enzymatic hydrolysis of dextrin and/or polyglucose and of the optional hydrogenation, by removing as much as possible the low molecular weight molecules present in the said products, it being possible for these molecules to consist for example of glucose, maltose or low molecular weight oligosaccharides, or of their possible hydrogenated equivalents.

These low molecular weight molecules can be removed for example by chromatographic separation on cationic resins converted to the alkali metal or alkaline-earth metal form or on zeolites, or they may be removed by processes such as membrane techniques such as ultrafiltration or reverse osmosis or by precipitation using solvents such as for example alcohols.

By virtue of the expected action within the scope of the present invention of an enzyme hydrolyzing the 1–6 bonds of amylopectin, polysaccharides are obtained which are much less digestible than the polysaccharides obtained following an enzymatic hydrolysis not comprising the additional action of this enzyme.

In order to characterize the digestibility of the polysaccharides obtained using the process conforming to the invention, the concentration of polysaccharides which are not digested by amyloglucosidase may be determined in an F test.

This test corresponds to the test for the determination of "total food fiber" developed by the company SIGMA Chemical Company, P.O. Box 14508, St. Louis,, Mo. 63178 USA. It is described in SIGMA technical note No. TDFAB-A of June 1991.

This test consists essentially in determining the amount of material contained in the hydrolysate which is not hydrolyzed by an amyloglucosidase in the presence of a thermo resistant α-amylase and a protease. This amount is expressed in percentage relative to an amount of about 1 g of hydrolysate previously dried under vacuum at 70° C., overnight.

To carry out this test, the procedure is as follows:

1) Four samples of about 1 g of hydrolysate previously dried on vacuum and cooled in a desiccator overnight, are weighed to within 0.1 mg and are transferred into a 400 ml tall-shaped beaker.

2) 50 ml of a phosphate buffer (0.05M) at pH: 6.0, is added to each of the four beakers.

3) 0.05 ml of a solution of alpha-amylase (Sigma product No. A 3306) is added to each of the beakers and mixed thoroughly.

4) Each beaker is covered with an aluminium foil being placed in a boiling water bath in order to incubate them for 30 min starting from the moment when the temperature in the beakers reaches 95° C. The mixture is stirred gently at regular 5 minute intervals.

5) The solutions are cooled to room temperature.

6) The pH of the solutions is adjusted to 7.5±0.1 by adding to each beaker 10 ml of 0.171N NaOH. The pH is checked and it is adjusted where appropriate with sodium hydroxide (0.171N) or phosphoric acid (0.205M).

7) 5 mg of protease powder (Sigma product No. P-3910) added to each of the beakers.

8) The beakers are covered with an alumminium foil and they are incubated at 60° C. for 30 min, with continuous stirring. The incubation time of 30 min starts from the moment when the internal temperature of the beakers reaches 60° C.

9) The mixture is cooled to room temperature.

10) 10 ml of 0.205M $H_3PO_4$ are added to each of the beakers in order to adjust the pH to 4.5±0.2. The pH is checked. It is carefully adjusted where appropriate with the sodium hydroxide or phosphoric acid solutions.

11) 0.3 ml of amyloglucosidase (Sigma product No. A. 9913) is added to each beaker.

12) Each of the beakers is covered with an aluminium foil and incubated for 30 minutes at 60° C., with continuous stirring. The incubation time of 30 min starts from the moment when the internal temperature of the beakers reaches 60° C.

13) 280 ml of 95% ethanol (v/v), preheated to 60° C., are added to each of the beakers. (95% ethanol v/v: 50 ml of demineralized water, pure alcohol complement to 1000 ml at 20° C.).

14) A precipitate is allowed to form by allowing the mixtures to stand at room temperature for at least 60 minutes, or overnight (the same time for each of the 4 tests).

15) The contents of each of the beakers are filtered under vacuum on a sintered glass crucible and Celite bed, and they are successively and carefully washed with:

three times 20 ml of 78% ethanol (v/v) (78% ethanol v/v: 220 ml of demineralized water, pure ethanol complement to 1000 ml at 20° C.)

two times 10 ml of 95% ethanol (v/v)

and two times 10 ml of acetone.

16) The four filters are dried overnight at 70° C. under vacuum.

17) These filters are cooled in a desiccator being weighed to within 0.1 mg, this weight being regarded as the sum of the weight of the filtration residue (polysaccharides not hydrolyzed by amyloglucosidase, plus proteins plus ash) and the weight of the crucible with Celite.

18) The protein concentrations of two of the four filtration residues resulting from the four tests are determined by proceeding according to the Kjeldahl method, using a correction factor of 6.25.

19) The amounts of ash on the other two filtration residues are determined by placing the crucibles in an oven at 525° C. for 5 hours.

20) The amounts of polysaccharides not hydrolyzed by amyloglucosidase are calculated for the four tests as indicated in the SIGMA technical note and a mean is calculated for these amounts which is expressed in terms of the mean of the amounts of hydrolysate material dried at 70° C. under vacuum, taking into account in the calculation the results of the four blank tests (without dry hydrolysate) carried out in parallel.

This F test constitutes a variant of the test for the determination of "total food fibers" in foodstuffs described in "J. Assoc. Off. Anal. Chem." Vol 68, No. 2, 1985, p 399.

It has the advantage of being standardized, of being able to be carried out using a complete analytical kit, and of being repeatable and reproducible.

This being the case, the digestibility of the polysaccharides obtained using the process conforming to the invention can also be characterized by determining the concentration of polysaccharides which can be precipitated in ethanol and are not hydrolyzed by amyloglucosidase, in another test called A.

In order to determine this concentration, the procedure is carried out as follows.

A sample of 10 g of dextrin hydrolysate optionally hydrogenated and optionally enriched, for example by chromatography, is adjusted to a Brix of 75±0.2, equivalent to a refractive index of about 1.478, before being used for the determination of the level of polysaccharides which can be precipated in ethanol.

The sample of 10 g of H.S.H at 75 Brix is supplemented with 30 cm$^3$ of distilled water and 60 cm$^3$ of absolute ethanol. The mixture is allowed to stand for 1 hour at 0° C. It is then centrifuged at 0° C. for 15 minutes at 10,000 g.

The pellet obtained is dried in a vacuum oven maintained at 80° C.

The weight of precipitate obtained, $p_1$, represents the weight of polysaccharides which can be precipitated in ethanol, contained in the 10 g of initial sample, equivalent to about 7.5 g of dry matter.

In order to determine the concentration in the hydrolysate of polysaccharides which can be precipitated in ethanol and are not hydrolyzed by amyloglucosidase, an A test is used which consists in subjecting the ethanol-precipitated polysaccharides obtained above to an enzymatic attack using a thermo resistant α-amylase, a protease and an amyloglucosidase, and then in precipitating the polysaccharides which are not hydrolyzed with 95% ethanol, in filtering the precipitate thus obtained, in washing the latter several times with alcohol and acetone, and finally in determining the weight, $P_2$, of the residue obtained.

This test is described in "J. Assoc. Off. Anal. Chem." vol. 68, No. 2, 1985, p. 399, to which reference may be made.

The fraction of polysaccharides which are not digested by amyloglucosidase becomes substantially increased relative to the concentration of high molecular weight polysaccharides when the enzymatic treatment of the same dextrin is carried out in the presence of an enzyme hydrolyzing the 1–6 bonds of amylopectin, compared with a treatment without using this enzyme. This quite obviously constitutes an important advantage of the invention, the polysaccharides, hydrogenated or otherwise, thus obtained thus possessing the optimal qualities of soluble food fibers.

The product obtained using the process conforming to the invention may be used as slightly hygroscopic and slightly calorific filling substance, medium for drying or substitute for sugar, fats, polyols or other ingredients in all types of food, pharmaceutical or dietary applications, alone or in combination with other products.

Indeed, they exhibit excellent compatibility with most food, pharmaceutical or dietary ingredients and may be optionally premixed, without any problem, with a preservative, an emulsifier, a sugar, a polyol such as xylitol, erythritol, mannitol, sorbitol and maltitol, a flavoring, an intense sweetener, an acid, an amino acid, a protein, a fat, an inorganic or organic filler such as sodium, potassium or calcium salts, polydextroses, fibers, fructooligosaccharides, gums, with an organic or inorganic gelling agent such as pectins, celluloses, algae and seed extracts, bacterial polysaccharides, with a raising agent, a vitamin, a pharmaceutical or veterinary ingredient.

Because of their high solubility in water, their specific organoleptic characteristics, their excellent stability to heat, to moisture and to the other ingredients of the formulation, and finally their remarkable metabolic properties, including in particular their very low digestibility, the products obtained using the process conforming to the invention may be advantageously used, in the form of a syrup or a powder, in the preparation of confectionary and chocolate products such as for example chewing gums, sweets, cereal bars and low-fat chocolates, in the preparation of milk products such as custard tarts, yoghurts, dessert mousses and dessert creams, in the preparation of extruded products of the snack or breakfast cereal type, in the preparation of frozen or deep-frozen products such as sherbets, prepared meals, in the preparation of meat products such as pâtés, in that of products derived from the processing of cereals or fruits such as pasta, crisp bread, cakes, jams and side dishes, and also in the preparation of drinks and food, dietary or pharmaceutical syrups.

Furthermore, because of their very high stability to microbial enzymes, the products obtained by virtue of the process conforming to the invention can also be used in cosmetics such as for example in the formulation of eye shadows, or incorporated in industrial products after having been optionally chemically or thermally modified.

EXAMPLES OF IMPLEMENTATION OF THE PROCESS CONFORMING TO THE INVENTION

EXAMPLE 1

Into a 25-liter tank, stirred and thermostatted, are introduced 20 liters of a syrup formed by diluting in water, to a dry matter content of 30%, the yellow dextrin TACKIDEX DF 165 marketed by the applicant company.

The pH of this syrup is adjusted to 5.5 and the temperature to 55° C. and then 0.015% (weight/dry weight) of the β-amylase SPEZYME DBA from GENENCOR and 0.2% (weight/dry weight) of the pullulanase PULLUZYME 750 L from ABM, are added.

After 72 hours, the mixture is acidified to pH 3.5 and the tank is heated at 80° C. for 20 minutes in order to inhibit the enzymes.

This syrup is then filtered and then demineralized over a strong cationic and weak anionic resin, and then it is subjected to a treatment with hydrogen peroxide (1.0% volume/volume) using a solution of $H_2O_2$ at 35% (v/v) for 24 hours at 70° C. and pH 9.5. A small amount of catalase is then added thereto in order to decompose the excess hydrogen peroxide and after degassing under vacuum, this syrup is treated with activated carbon and then over a bed of mixed resins before concentrating it to a dry matter content of 75%.

This syrup has a concentration of polysaccharides not digested by amyloglucosidase according to the F test, of 16.2%, an alcohol precipitate $p_1$ according to the A test of 38% and a precipitate $P_2$ of 7.6% according to the same test, and has completely acceptable organoleptic properties.

EXAMPLE 2

Into a 25-liter tank, stirred and thermostatted, are introduced 20 liters of a syrup formed by diluting in water, to a dry matter content of 35%, the yellow dextrin TACKIDEX DF 165. The pH of this syrup is adjusted to 5.5 and the temperature to 55° C., and then the following are introduced:
Hydrolysates 2a and 2b: 0.15% (w/dry w) of the β-amylase, Spezyme DBA from Genencor and 0.2% (w/dry w) of the pullulanase Pulluzyme 750 L from ABM.
Hydrolysate 2c (according to the prior art): 0.15% (w/dry w) of the β-amylase Spezyme DBA from Genencor.

After 24 hours, 0.1% (w/dry w) of the α-amylase Maxamyl HT 3000 from Gist is added to the hydrolysates 2b and 2c.

After 86 hours, the mixture is acidified to pH 3.5 and the tank is heated at 80° C. for 20 minutes in order to inhibit the enzymes. These syrups are then filtered and then demineralized over strong cationic and weak anionic resins and finally concentrated to 75% DM content.

These syrups exhibit the carbohydrate spectra given in Table I.

The hydrolysate 2a is used to prepare a hydrogenated syrup. For this purpose, its dry matter content is adjusted to 40%. 5% of Raney nickel catalyst is added relative to the syrup. The hydrogenation is carried out at a temperature of 130° C. at a hydrogen pressure of 50 bars. It is continued until a reducing sugar level of less than 0.5% is obtained.

The hydrolysate thus obtained (hydrolysate 2aH) is then purified and concentrated to 75% DM content. It contains about 1% of sorbitol, 22% of maltitol and isomaltitol and 25%, relative to its dry matter, of polysaccharides which are not hydrolyzed according to the F test.

TABLE I

| COMPOSITION IN % | EXAMPLES ACCORDING TO THE INVENTION | | COMPARATIVE EXAMPLE |
|---|---|---|---|
| | Hydrolysate 2a | Hydrolysate 2b | HYDROLYSATE 2c |
| DP1 | 0.7 | 1.3 | 1.1 |
| DP2 | 22.3 | 22.0 | 19.3 |
| DP3 | 6.1 | 6.2 | 5.0 |
| DP4 | 3.8 | 3.5 | 3.3 |
| DP5 | 4.3 | 4.3 | 4.7 |
| DP6 | 3.6 | 4.6 | 4.3 |
| DP7 | 4.0 | 3.9 | 3.8 |
| DP 8 to 20 | 28.2 | 28.8 | 28.6 |
| DP > 20 | 27.0 | 28.4 | 29.9 |
| F Value in % (concentration according to the F test of polysaccharides not hydrolyzed by amyloglucosidase) | 26.1 | 23.8 | 27.2 |
| $\frac{\text{F value}}{\text{DP} > 20}$ in % | 96.7 | 93.7 | 90.9 |

The compositions according to the invention have a higher maltose concentration than the composition of the prior art.

Furthermore, they have lower concentrations of polysaccharides which are not hydrolyzed by amyloglucosidase relative to the dry matter of the hydrolysates, but increased relative to the amounts of high molecular weight polysaccharides in the hydrolysates.

EXAMPLE 3

Into a 25-liter tank, stirred and thermostatted, are introduced 20 liters of a syrup formed by diluting in water, to a dry matter content of 35%, the yellow dextrin TACKIDEX DF 165. The pH of this syrup is adjusted to 5.5 and the temperature to 55° C., and then the following are introduced:
Hydrolysate 3a: 0.15% (w/dry w) of the amyloglucosidase Amigase TS 300 from GIST, 0.2% (w/dry w) of the pullulanase Pulluzyme 750 L from ABM and 0.15% (w/dry w) of the α-amylase Maxamyl HT 3000 from GIST.
Hydrolysate 3b: 0.15% (w/dry w) of the amyloglucosidase Amigase TS 300 and 0.2% (w/dry w) of the pullulanase Pulluzyme 750 L from ABM.
Hydrolysate 3c (according to the prior art): 0.1% (w/dry w) of the fungal α-amylase MKC LF 40 from Miles.

After 86 hours, the mixture is acidified to pH=3.5 and the tank is heated at 80° C. for 20 minutes in order to inhibit the enzymes.

These syrups are then filtered, demineralized over strong cationic and weak anionic resins and concentrated to 75% DM content. A portion of the hydrolysate 3a is hydrogenated as described in example 2 (hydrolysate 3aH). The hydrolysate 3aH contains about 36.5% of sorbitol.

The carbohydrate spectra of the hydrolysates 3a, 3b and 3c are presented in Table II below:

TABLE II

| COMPOSITION IN % | EXAMPLES ACCORDING TO THE INVENTION | | COMPARATIVE EXAMPLE |
|---|---|---|---|
| | 3a | 3b | 3c |
| DP1 | 35.3 | 34.5 | 32.4 |
| DP2 to DP20 | 46.3 | 46.2 | 41.7 |
| DP > 20 | 18.4 | 19.3 | 25.9 |

The products according to the invention are higher in glucose and lower in polysaccharides than the hydrolysate according to the prior art.

The hydrolysates 3b and 3c are mutually compared at 10% DM content by a test panel according to a triangular test. The differences between the two products are not significant.

The two products are judged to be neutral in taste, not very sweet and not bitter. The hydrolysate 3aH also has excellent organoleptic properties.

EXAMPLE 4

Into a 25-liter tank, stirred and thermostatted, are introduced 20 liters of a syrup formed by diluting in water, to a dry matter content of 35%, the yellow dextrin of the trademark TACKIDEX DF 165.

The pH of this syrup is adjusted to 5.5 and the temperature to 55° C. and then the following are introduced:
hydrolysate 4a
0.15% (w/dry w) of the amyloglucosidase Amigase TS 300 from GIST
0.2% (w/dry w) of the pullulanase Pulluzyme 750 L from ABM and
0.15% (w/dry w) of the α-amylase Maxamyl HT 3000 from GIST.
Hydrolysate 4b (according to the prior art)

1.0 % (w/dry w) of the fungal α-amylase MKC LF40 from Miles.

After 86 hours, the mixture is acidified to pH=3.5 and the temperature of the tank is increased to 80° C. for 20 minutes in order to inhibit the enzymes.

The two hydrolysates are then filtered, and then chromatographed over a cationic sodium resin according to the usual industrial conditions.

The fractions high in high molecular weight are recovered and are purified and spray-dried (powders 4a and 4b).

The powder 4a is redissolved to 40% DM content and then the syrup obtained is hydrogenated, purified and spray-dried (powder 4aH).

Compositions

The carbohydrate spectra for the products 4a and 4b are given in Table III.

TABLE III

| COMPOSITIONS IN % | Powder 4a (invention) | Powder 4b (according to the prior art) |
| --- | --- | --- |
| DP 1 to DP 5 | 10.7 | 7.7 |
| DP 6 and DP 7 | 10.6 | 8.5 |
| DP 8 to DP 20 | 39.4 | 35.2 |
| DP > 20 | 39.3 | 48.6 |
| F value in % (polysaccharides not hydrolyzed by amyloglucosidase according to the F test) | 47.6 | 46.4 |
| $\frac{F\ value}{DP > 20}$ in % | 121 | 95 |

The powder 4aH contains 44.1% of polysaccharides which are not hydrolyzed by amyloglucosidase according to the F test and a hydrogenated mono-, di-, tri-, oligo- and polysaccharide composition which is very similar in percentage terms to the composition of the non hydrogenated powder 4a.

Organoleptic properties

Taste

The powders 4a and 4aH are compared in taste to the polydextroses A, K and Litesse® from the company Pfizer. The tastings are carried out on solutions at 20% DM content light yellow for the syrup polydextrose A orange colored for the syrup Litesse® dark orange for the syrup polydextrose K

If the syrups 4a and 4aH are compared, it is observed that the hydrogenation has had only a very slight beneficial effect. The products 4a and 4aH, which are neutral in color, may be suitable for the preparation of food or dietary drinks.

Physico chemical properties viscosity

The syrups 4a and 4aH at 70% DM content have a viscosity of 14,500 and 12,200 cps respectively.

They are more viscous than the polydextrose syrups at the same dry matter content (1,200 to 1,600 cps). The powders 4a and 4aH are excellent viscosity-promoting and thickening agents. They can therefore be used for controlling the crystallization of other products.

The viscosity of the syrups 4a and 4aH can be reduced by adding a low molecular weight molecule (glycerol, sorbitol or xylitol). In such a case, they can be more highly concentrated (up to 92% dry matter content) and used as plasticizing and binding agents.

Water activity and hygroscopicity

At 70% DM content, the syrups 4a and 4aH have a water activity in the region of 0.90 against about 0.88 for the polydextrose syrups.

In other words, for the same dry matter, the products according to the invention are less hygroscopic and reduce the freezing points of water to a lesser extent.

The addition of a salt, a sugar or a polyol makes it possible easily to adjust these water activity values, thus making it possible to use these syrups in the preparation of ice creams, frozen desserts, deep-frozen products, bakery, biscuit and pastry products.

The powders 4a and 4aH preserve the same pulverulent state during storage as that of freshly spray-dried powders. They are particularly non hygroscopic and may therefore be suitable as medium for drying for example vitamins, flavorings, coloring, intense sweeteners or as powdering agent, antisticking agent, anticaking agent or gumming agent.

Stability to boiling

The syrups 4a, 4aH and Litesse® are concentrated in order to manufacture boiled sugars by boiling at 130° C. The

| | Syrups at 20% DM content | | | | |
| --- | --- | --- | --- | --- | --- |
| | Powder 4a | Powder 4aH | Polydextrose A | Polydextrose K | Litesee ® |
| Taste | Neutral Not sweet Not bitter No aftertaste | Neutral Not sweet Not bitter No aftertaste | Very sour bitter existence of an aftertaste | Very slightly sweet and salty bitter existence of an aftertaste | Very slightly sweet slightly bitter slight aftertaste |

The products according to the process conforming to the invention are judged to be excellent in taste. They are neutral and can therefore be used in unsweetened food stuffs, but also in foodstuffs sweetened by the addition of a mass (sugar, polyols) or intense (aspartame, alitame, acesulfame) sweetener.

Colors in solution

The various solutions at 20% DM content are concentrated to 70% DM content by boiling.

The solutions are:

very slightly colored for the syrups 4aH and 4a final product obtained with the syrup 4aH is by far the least colored. The products conforming to the invention are very stable, in particular the hydrogenated product 4aH. This is particularly important and makes it possible to use these syrups for the preparation of boiled products such as confectionary items.

Stability to enzymes

The syrups 4a and 4aH, in particular the syrup 4aH, are more stable than the polydextroses to the enzymes present in the buccal cavity.

The syrup 4aH is not cariogenic.

EXAMPLE 5: LOW CALORIFIC AND SUGAR-FREE CHEWING GUMS CONTAINING SOLUBLE INDIGESTIBLE POLYSACCHARIDES

Chewing gums of the bubble-gum type are prepared containing polysaccharides of low digestability obtained by the process according to the invention.

For this purpose, the following procedure, which makes it possible to obtain 3 kg of chewing gum paste, is followed.

Two sweetening premixes are first prepared:

the first contains 585 g of the sorbitol powder Neosorb$^R$ P 100 T marketed by the applicant company, 585 g of the powder 4aH according to the invention, 27 g of ground malic acid and 9 g of ground citric acid.

the second contains 270 g of the xylitol Xylisorb® marketed by the applicant company, 10 g of aspartame, 100 g of ground erythritol, 160 g of the powder 4aH according to the invention and 24 g of orange flavoring.

780 g of bubble-gum gum base, previously softened (obtained from the company Cofosa) are subsequently introduced into a "Z"-shaped arm type kneading machine heated to 50° C.

Half of the amount of the first premix is then added while continuing to knead for 2 min. 225 g of the hydrolysate 2aH are then introduced.

After kneading for one minute, the second half of the first premix is added and the mixture is again kneaded for 2 min before incorporating 225 g of the maltitol syrup Lycasin® 80/55 at 85% DM content, marketed by the applicant company.

Finally, the second premix is added after mixing for a further two minutes. The mixture is blended for a further three minutes.

After this, the mixture is flattened and the chewing gum paste obtained is shaped using as dusting powder nonhygroscopic talc, a mixture based on 6.9 g of mannitol, 3.0 g of the powder 4aH according to the invention and 0.1 g of acesulfame K.

Soft and non-sticky chewing gums with a very nice taste are obtained in this manner, containing about 12% of indigestible polysaccharides.

During storage, these chewing gums remain soft and do not tend to regain water. The soluble, indigestible polysaccharides incorporated into these chewing gums act as a nonhygroscopic anticrystallizing agent. They may therefore be suitable for all types of chewing gums, whether containing water or not.

I claim:

1. A process for preparing indigestible polysaccharides which comprises enzymatically hydrolyzing, with at least one saccharifying enzyme selected from the group consisting of β-amylase and amyloglucosidase, and at least one enzyme which hydrolyzes the 1–6 bonds of amylopectin, selected from the group consisting of isoamylase and pullulanase has been inserted at least one dextrin, said dextrin being obtained by dry roasting of starch in the presence of an acid or basic catalyst to obtain a D.E. of about 0.5 to 10, or one polyglucose, said polyglucose being a product predominantly composed of 1–6 bonds and obtained by condensation or rearrangement from glucose or from one or more optionally reduced sugars under the combined action of heat and acids in a medium substantially free of water, and then recovering said indigestible polysaccharides.

2. The process according to claim 1, wherein the enzymatic hydrolysis is performed such that a DE between 5 and 80 is obtained.

3. The process according to claim 1, wherein the enzymatic hydrolysis of the dextrin or the polyglucose comprises the additional action of an α-amylase.

4. The process according to claim 1, wherein the enzymatic hydrolysis of the dextrin or the polyglucose is preceded by an acid hydrolysis.

5. The process according to claim 1, wherein the conditions for the action of the various enzymes are selected from the following:

β-emylase: 100 to 10,000 LINTNER units/kg of dry substrate, temperature of 50° C. to 60° C., duration of action from 30 to 100 hours, pH of 5.0 to 6.0;

amyloglucosidase: 4,000 to 500,000 international units/kg of dry substrate, temperature of 50° C. to 60° C., duration of action from 30 to 100 hours, pH of 5.0 to 6.0;

enzyme hydrolyzing the 1–6 bonds of amylopectin: 150 to 15,000 ABM units/kg of dry substrate, pH of 5.0 to 6.0, temperature of 50° C. to 60° C., duration of action from 24 to 100 hours;

α-amylase : 20 to 2,000 KNU units/kg of dry substrate, pH of 5.0 to 6.0, temperature of 50° C. to 60° C., duration of action from 16 to 100 hours.

6. The process according to claim 1, wherein the product obtained following the enzymatic hydrolysis of the dextrin or the polyglucose is hydrogenated.

7. The process according to claim 6, wherein the hydrogenation is carried out until a percentage ratio of residual sugars to dry matter of less than 2.0 is obtained.

8. The process according to claim 6, wherein the hydrogenation is carried out until a percentage ratio of residual sugars to dry matter of less than 1.0 is obtained.

9. The process according to claim 6, wherein the hydrogenation is carried out until a percentage ratio of residual sugars to dry matter of less than 0.25 is obtained.

10. In a food product containing indigestible polysaccharides, the improvement wherein said indigestible polysaccharides comprise indigestible polysaccharides produced by the process of claim 1.

11. In a pharmaceutical product containing indigestible polysaccharides, the improvement wherein said indigestible polysaccharides comprise indigestible polysaccharides produced by the process of claim 1.

12. In a dietary product containing indigestible polysaccharides, the improvement wherein said indigestible polysaccharides comprise indigestible polysaccharides produced by the process of claim 1.

13. In a chewing gum product containing indigestible polysaccharides, the improvement wherein said indigestible polysaccharides comprise indigestible polysaccharides produced by the process of claim 1.

14. In a cosmetic product containing indigestible polysaccharides, the improvement wherein said indigestible polysaccharides comprise indigestible polysaccharides produced by the process of claim 1.

15. In an industrial product containing indigestible polysaccharides, the improvement wherein said indigestible polysaccharides comprise indigestible polysaccharides produced by the process of claim 1.

* * * * *

UNITED STATES PATENT AND TRADEMARK OFFICE
CERTIFICATE OF CORRECTION

PATENT NO.  : 5,620,871
DATED       : April 15, 1997
INVENTOR(S) : CABOCHE, Jean-Jacques It is certified that error appears in the above-indentified patent and that said Letters Patent is hereby corrected as shown below:

Title page: item [73] should read as follows:

--[73] Assignee: Roquette Freres, Lestrem, France--.

Column 13, line 56, delete "has been inserted--.

Column 14, line 13, delete "$\beta$-emylase" and insert --$\beta$-amylase--.

Signed and Sealed this

Sixth Day of January, 1998

*Attest:*

*Attesting Officer*

BRUCE LEHMAN

*Commissioner of Patents and Trademarks*